(12) United States Patent
Paraskos et al.

(10) Patent No.: US 7,763,753 B1
(45) Date of Patent: Jul. 27, 2010

(54) METHODS FOR THE PRODUCTION OF 1,3,5-TRIAMINO-2,4,6-TRINITROBENZENE

(75) Inventors: Alexander J. Paraskos, Ogden, UT (US); Michael P. Kramer, Wellsville, UT (US)

(73) Assignee: Alliant Techsystems Inc., Minneapolis, MN (US)

( * ) Notice: Subject to any disclaimer, the term of this patent is extended or adjusted under 35 U.S.C. 154(b) by 0 days.

(21) Appl. No.: 12/484,917

(22) Filed: Jun. 15, 2009

(51) Int. Cl.
C07C 209/18 (2006.01)

(52) U.S. Cl. .................................................. 564/399

(58) Field of Classification Search ....................... None
See application file for complete search history.

(56) References Cited

U.S. PATENT DOCUMENTS

| | | | |
|---|---|---|---|
| 1,380,186 A | 5/1921 | Brewster |
| 1,396,001 A | 11/1921 | MacDonald |
| 2,246,963 A | 6/1941 | Wilkinson |
| 3,278,604 A | 10/1966 | Hoffman et al. |
| 3,394,183 A | 7/1968 | Dacons et al. |
| 3,933,926 A | 1/1976 | Salter et al. |
| 3,954,852 A | 5/1976 | Shen et al. |
| 4,032,377 A | 6/1977 | Benziger |
| 4,232,175 A | 11/1980 | Smith et al. |
| 4,434,304 A | 2/1984 | DeFusco, Jr. et al. |
| 4,745,232 A | 5/1988 | Schmitt et al. |
| 4,952,733 A | 8/1990 | Ott et al. |
| 4,997,987 A | 3/1991 | Ott et al. |
| 5,371,291 A | 12/1994 | Nader |
| 5,569,783 A | 10/1996 | Mitchell et al. |
| 5,633,406 A | 5/1997 | Mitchell et al. |
| 6,069,277 A | 5/2000 | Mitchell et al. |
| 7,057,072 B2 | 6/2006 | Mitchell et al. |
| 7,057,073 B2 | 6/2006 | Mitchell et al. |

FOREIGN PATENT DOCUMENTS

| | | | |
|---|---|---|---|
| GB | 2355715 A | | 5/2001 |
| GB | 2355714 B | * | 3/2004 |
| WO | 9419310 A1 | | 9/1994 |

OTHER PUBLICATIONS

Agrawal, J.P., et al., Organic Chemistry of Explosives, pp. 142-143, © 2007, John Wiley & Sons Ltd., West Sussex, England.
Bellamy, A., et al., "Nitration of 1,3,5-trimethoxybenzene," J. Chem. Research (S), pp. 412-413, 2002.
Bellamy, A., et al., "Nitration of 1,3,5-trimethoxybenzene," J. Chem. Research (M), pp. 0919-0930, 2002.
Bellamy, Anthony J., et al., "A New Synthetic Route to 1,3,5-Triamino-2,4,6-Trinitrobenzene (TATB)," Propellants, Explosives, Pyrotechnics, vol. 27, pp. 49-58, 2002.
Bellamy, Anthony J., et al., "Synthesis of Ammonium Diaminopicrate (ADAP), a New Secondary Explosive," Propellants, Explosive, Pyrotechnics, vol. 27, pp. 59-61, 2002.
Bose, P.C., et al., "Occurrence of Dehydrorotenone in *Derris uliginosa* Benth," Indian J. Chem., vol. 14B, pp. 1012-1013, Dec. 1976.
DeFusco, A.A., et al., "An Improved Preparation of Trinitrophloroglucinol," Organic Preparations and Procedures Int., vol. 14, No. 6, pp. 393-424, 1982.
Dobratz, Brigitta M., "The Insensitive High Explosive Triaminotrinitrobenzene (TATB): Development and Characterization—1988 to 1994," Los Alamos Nat'l. Lab., LA-13014-H, History, UC-741, 151 pages, Aug. 1995.
Dove, Michael F.A., et al., "Vanadium(v) oxytrinitrate, VO(NO3)3. A powerful reagent for the nitration of aromatic compounds at room temperature under non-acidic conditions," J. Chem. Soc., Perkin Trans. 1, pp. 1589-1590, 1998.
Hoffman, D. Mark, et al., "Comparison of New and Legacy TATBs," Journal of Energetic Materials, vol. 26, pp. 139-162, 2008.
Hofmann, K.A., et al., "Verbindungen von Kobaltnitriten mit p-Toluidin, Diazoaminotoluol, Hydrazin und Nitrosohydrazin," Miteilung a. d. Chem. Laborat. D. Kgl. Akad. D. Wissenschafter zu Munchen, Eingengangen am Aug. 14, 1908, pp. 3084-3090.
Maiti, A., et al., "Solvent screening for a hard-to-dissolve molecular crystal," Physical Chemistry Chemical Physics, vol. 10, pp. 5050-5056, 2008.
Majumdar, M.P., et al., "Nitration of Organic Compounds with Urea Nitrate-Sulphuric Acid," Indian J. Chem., vol. 14B, pp. 1012-1013, Dec. 1976.
Mehilal, et al., "Studies on 2,4,6-trinitrophloroglucinol (TNPG)—A novel flash sensitizer," Indian Journal of Engineering & Materials Sciences, vol. 11, pp. 59-62, Feb. 2004.
Mellor, John M., et al., "Improved Nitrations Using Metal Nitrate—Sulfuric Acid Systems," Tetrahedron, vol. 56, pp. 8019-8024, 2000.
Mitchell, Alexander R., et al., "A New Synthesis of TATB Using Inexpensive Starting Materials and Mild Reaction Conditions," prepared for submittal to the 27th International Annual Conference of ICT, Jun. 25-28, 1996, Karlsruhe, Federal Republic of Germany, 14 pages, Apr. 1996.
Olah, George A., et al., "New Synthetic Reagents and Reactions," Aldrichimica Acta, vol. 12, No. 3, pp. 43-49, 1979.
Olah, George A., et al., Nitration Methods and Mechanisms, © 1989 VCH Publishers, Inc., New York, NY, p. 29.
Ott, D.G., et al., "Preparation of 1,3,5-Triamino-2,4,6-Trinitrobenzene from 3,4-Dichloroanisole," Journal of Energetic Materials, vol. 5, pp. 343-354, 1987.
Schmidt, Robert D., et al., "New Synthesis of TATB. Process Development Studies," prepared for submittal to the JOWOG 9 (Joint Working Group 9), Aldermaston, England, Jun. 22-26, 1998, 14 pages, May 1998.

(Continued)

*Primary Examiner*—Brian J Davis
(74) *Attorney, Agent, or Firm*—TraskBritt

(57) ABSTRACT

Methods of producing 1,3,5-triamino-2,4,6-trinitrobenzene are disclosed. One method comprises dissolving a 1,3,5-trialkoxy-2,4,6-trinitrobenzene compound in an organic solvent to form a 1,3,5-trialkoxy-2,4,6-trinitrobenzene compound solution. The 1,3,5-trialkoxy-2,4,6-trinitrobenzene compound solution is heated to a temperature of from approximately 30° C. to approximately 110° C. The 1,3,5-trialkoxy-2,4,6-trinitrobenzene compound is reacted with an aminating agent at a pressure of from approximately 30 pounds per square inch to approximately 120 pounds per square inch to produce a 1,3,5-triamino-2,4,6-trinitrobenzene solution.

16 Claims, 2 Drawing Sheets

OTHER PUBLICATIONS

Smith, Bengt, "The Reaction between Phenols and Orthoesters. A New Synthesis of Aryl Alkyl Ethers," Acta Chem. Scand., vol. 10, No. 6, pp. 1006-1010, 1956.

Waller, Francis J., et al., "Lanthanide(III) and Group IV metal triflate catalysed electrophilic nitration: 'nitrate capture' and the role of the metal centre," J. Chem. Soc., Perkin Trans. 1, pp. 867-871, 1999.

Zolfigol, Mohammad Ali, et al., "Nitration of Aromatic Compounds on Silica Sulfuric Acid," Bull. Korean Chem. Soc., vol. 25, No. 9, pp. 1414-1416, 2004.

Zolfigol, Mohammad Ali, et al., "Silica Sulfuric Acid/ NaNO2 as a Novel Heterogeneous System for the Nitration of Phenols under Mild Conditions," Molecules, vol. 7, pp. 734-742, 2002.

Velarde et al., U.S. Appl. No. 11/744,986, filed May 7, 2007, entitled, "Methods of Producing 1,3,5-Triamino-2,4,6-Trinitrobenzene".

Schedule of 2008 GRC on Energetic Materials, Jun. 16-18, 2008, 5 pages.

Straessler et al., U.S. Appl. No. 12/484,985, filed Jun. 15, 2009, entitled, "Methods of Producing 1,3,5-Triamino-2,4,6-Trintrobenzene."

Straessler et al., U.S. Appl. No. 12/484,960, filed Jun. 15, 2009, entitled, "Methods for Nitrating Compounds.".

http://en.wikipedia.org/wiki/Room_temperature, last visited Dec. 11, 2009.

* cited by examiner

METHODS FOR THE PRODUCTION OF 1,3,5-TRIAMINO-2,4,6-TRINITROBENZENE

CROSS-REFERENCE TO RELATED APPLICATIONS

This application is related to co-pending U.S. patent application Ser. No. 11/744,986 to Velarde et al., entitled "METHODS OF PRODUCING 1,3,5-TRIAMINO-2,4,6-TRINITROBENZENE," filed on May 7, 2007. This application is also related to co-pending U.S. patent application Ser. Nos. 12/484,985 entitled "METHODS OF PRODUCING 1,3,5-TRIAMINO-2,4,6-TRINITROBENZENE," and 12/484,960 entitled "METHODS FOR NITRATING COMPOUNDS," each of which was filed on even date herewith and assigned to the Assignee of the present application. The disclosure of each of the three above-mentioned applications is incorporated by reference herein in its entirety.

TECHNICAL FIELD

Embodiments of the present invention relate to methods of producing 1,3,5-triamino-2,4,6-trinitrobenzene ("TATB") and, more particularly, to methods of producing TATB from a 1,3,5-trialkoxy-2,4,6-trinitrobenzene compound, such as 1,3,5-triethoxy-2,4,6-trinitrobenzene ("TETNB").

BACKGROUND

TATB is an insensitive energetic material used in various military applications. TATB is used in warhead fuzes and also as the explosive component in insensitive high explosives, such as in plastic bonded explosive compositions. TATB has been produced from various starting materials, such as 1,3,5-trichlorobenzene, 3,5-dichloroanisole, 3,5-dibromoanisole, trinitrobenzene, picramide, or phloroglucinol. While various methods of producing TATB are known, TATB is no longer available from a qualified supplier for Department of Defense applications.

U.S. Pat. No. 4,032,377 to Benziger describes synthesizing TATB from 1,3,5-trichlorobenzene. The 1,3,5-trichlorobenzene is nitrated, producing 1,3,5-trichloro-2,4,6-trinitrobenzene ("TCTNB"), which is then aminated to produce TATB. In addition to TATB, ammonium chloride is produced as an impurity. The nitration and amination reactions are conducted at a temperature of 150° C. for an extended period of time. The pressure during the amination reaction is from 35 psig to 40 psig. The TATB produced by this process is referred to herein as so-called "legacy TATB." This process is currently qualified by the U.S. Department of Energy and the U.S. Department of Defense. However, the 1,3,5-trichlorobenzene starting material is toxic, and environmentally hazardous waste streams are produced in its manufacture, making it an ever increasingly less attractive material. As such, the production of 1,3,5-trichlorobenzene is currently conducted only outside of the United States, such as in China. With no domestic sources of 1,3,5-trichlorobenzene available, production of legacy TATB within the United States is an expensive prospect with an uncertain and unreliable source of starting material.

One method of synthesizing TATB from phloroglucinol is described in GB 2355715. Phloroglucinol, also known as 1,3,5-trihydroxybenzene, is nitrated using sodium nitrite and nitric acid, forming trinitrophloroglucinol ("TNPG"), which is also known as 1,3,5-trihydroxy-2,4,6-trinitrobenzene. The nitric acid is added sequentially or in multiple additions. When cooled, a solid is produced, which is filtered, washed with 3 M hydrochloric acid ("HCl"), and dried, yielding a solid product that is a monohydrate of TNPG. The monohydrate of TNPG is a free-flowing solid. The TNPG is alkoxylated using a trialkyl orthoformate, such as trimethyl orthoformate, forming 1,3,5-trimethoxy-2,4,6-trinitrobenzene. Methanol and methyl formate are also formed and are removed by distillation. The solution of 1,3,5-trimethoxy-2,4,6-trinitrobenzene is concentrated, yielding 1,3,5-trimethoxy-2,4,6-trinitrobenzene as a solid, which is recrystallized from ethanol. The purified 1,3,5-trimethoxy-2,4,6-trinitrobenzene is then aminated using liquid ammonia or gaseous ammonia, filtered, washed with N-methylpyrrolidinone and methanol, and dried, yielding crystals of the TATB. To conduct the amination reaction, a solution of the 1,3,5-trimethoxy-2,4,6-trinitrobenzene is cooled to −10° C. and ammonia gas is introduced. If liquid ammonia is used, the amination reaction is conducted at room temperature and a pressure of 8-9 bar, or at atmospheric pressure and −33° C. If gaseous ammonia is used, the amination reaction is conducted at atmospheric pressure or at a pressure of 8-9 bar. At higher temperatures, the method is described as being less energy efficient. The TATB synthesis utilizes multiple drying and isolation acts to produce solid products of TNPG, TETNB, and TATB.

Another method of synthesizing TATB from phloroglucinol is described in co-pending U.S. patent application Ser. No. 11/744,986 to Velarde et al., entitled "METHODS OF PRODUCING 1,3,5-TRIAMINO-2,4,6-TRINITROBENZENE." For convenience, this process is referred to herein as the "Velarde process" and the above-mentioned patent application is referred to herein as the "Velarde application." The TATB produced by this process is referred to herein as so-called "Velarde TATB." In the Velarde process, the phloroglucinol is nitrated to produce TNPG, which is then alkoxylated to produce a 1,3,5-trialkoxy-2,4,6-trinitrobenzene, such as 1,3,5-triethoxy-2,4,6-trinitrobenzene ("TETNB"). The 1,3,5-trialkoxy-2,4,6-trinitrobenzene is then aminated, producing TATB. TATB produced by this process possesses an amorphous, agglomerate crystal structure, has a purity of 98%-99% (as measured by high pressure liquid chromatography ("HPLC")), and has lower thermal stability (as measured by DSC onset) than legacy TATB. The amorphous, agglomerate structure of the TATB results in a low bulk density. Impurities produced during the process include ammonium diaminopicrate ("ADAP") salt and ethoxydiaminotrinitrobenzene ("EDATB"). The agglomerates of TATB are greater than approximately 50 μm in diameter and are formed from agglomerates of smaller-sized TATB, which decreases the sensitivity of the TATB.

One major difficulty associated with the synthesis of TATB results from its insolubility in most organic solvents, even at an elevated temperature. TATB is sparingly soluble in dimethyl sulfoxide ("DMSO") (i.e., 0.047% solution in DMSO at 21° C.), dimethylformamide ("DMF"), acetonitrile, and concentrated sulfuric acid. Due to this insolubility, TATB having the crystal structure or crystal morphology ultimately desired in the final product must be obtained as the result of the synthesis. If the incorrect crystal structure is obtained, recrystallization of the TATB to obtain the correct crystal morphology is not practical.

It would be desirable to synthesize TATB from an environmentally friendly starting material. The TATB produced may exhibit comparable purity, thermal stability, and crystal morphology as legacy TATB, and improved purity, thermal stability, and crystal morphology compared to TATB produced by other known processes.

BRIEF SUMMARY

Various embodiments of the invention comprise methods of producing 1,3,5-triamino-2,4,6-trinitrobenzene. One embodiment comprises a method of producing 1,3,5-triamino-2,4,6-trinitrobenzene wherein a 1,3,5-trialkoxy-2,4,6-trinitrobenzene compound is dissolved in an organic solvent to form a 1,3,5-trialkoxy-2,4,6-trinitrobenzene compound solution. The 1,3,5-trialkoxy-2,4,6-trinitrobenzene compound solution is heated to a temperature of from approximately 30° C. to approximately 110° C. The 1,3,5-trialkoxy-2,4,6-trinitrobenzene compound is reacted with an aminating agent at a pressure of from approximately 30 pounds per square inch to approximately 120 pounds per square inch to produce a 1,3,5-triamino-2,4,6-trinitrobenzene solution.

Another embodiment comprises a method of producing 1,3,5-triamino-2,4,6-trinitrobenzene wherein 1,3,5-triethoxy-2,4,6-trinitrobenzene is dissolved in toluene to form a 1,3,5-triethoxy-2,4,6-trinitrobenzene solution, which is heated to a temperature of approximately 90° C. The 1,3,5-triethoxy-2,4,6-trinitrobenzene is reacted with ammonia at a pressure of approximately 60 pounds per square inch to produce 1,3,5-triamino-2,4,6-trinitrobenzene.

Yet a further embodiment comprises a method of producing 1,3,5-triamino-2,4,6-trinitrobenzene wherein a 1,3,5-triethoxy-2,4,6-trinitrobenzene solution is introduced into a pressure vessel and the pressure vessel is sealed. The 1,3,5-triethoxy-2,4,6-trinitrobenzene solution is heated to a temperature of approximately 90° C. and the pressure vessel is pressurized with ammonia to a total reactor pressure of approximately 60 pounds per square inch. The 1,3,5-triethoxy-2,4,6-trinitrobenzene is reacted with the ammonia to produce 1,3,5-triamino-2,4,6-trinitrobenzene.

BRIEF DESCRIPTION OF THE DRAWINGS

While the specification concludes with claims particularly pointing out and distinctly claiming that which is regarded as the present invention, the advantages of this invention may be more readily ascertained from the following description of the invention when read in conjunction with the accompanying drawings in which:

DETAILED DESCRIPTION

Figure 1:
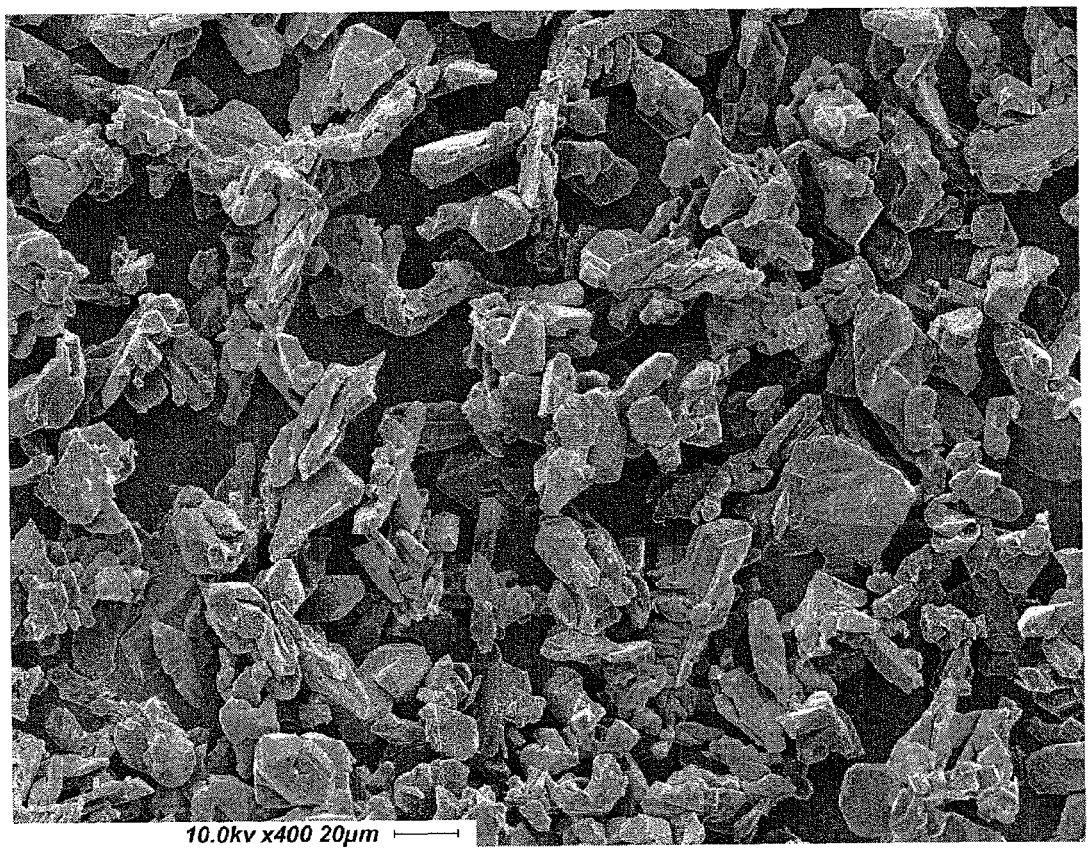
FIG. 1 is a scanning electron micrograph ("SEM") of TATB produced by an embodiment of the invention.

As used herein, the terms "comprising," "including," "containing," "characterized by," and grammatical equivalents thereof are inclusive or open-ended terms that do not exclude additional, unrecited elements or method acts, but also include the more restrictive terms "consisting of" and "consisting essentially of" and grammatical equivalents thereof. As used herein, the term "may" with respect to a material, structure, feature, or method act indicates that such is contemplated for use in implementation of an embodiment of the invention. This term is used in preference to the more restrictive term "is" so as to avoid any implication that other, compatible materials, structures, features, and methods usable in combination therewith should or must be, excluded.

A method of producing TATB from phloroglucinol is described. The method produces TATB having comparable purity, thermal stability, and crystal morphology compared to legacy TATB and improved purity, thermal stability, and crystal morphology compared to TATB produced by the Velarde process. A reaction scheme for producing TATB is shown below:

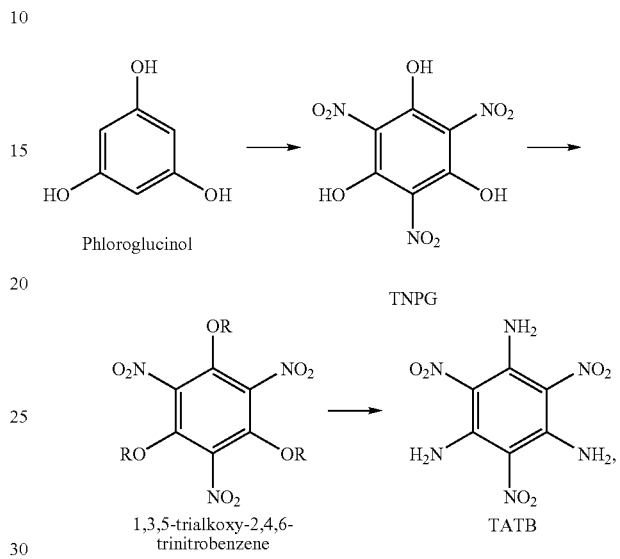

where R is an alkyl group including, but not limited to, a methyl, ethyl, or propyl group. While specific examples herein describe a compound where R is an ethyl group (i.e., TETNB), other alkyl groups may be used. The TNPG is produced by nitrating phloroglucinol using sodium nitrite, nitric acid, water, and a caustic solution, as described in the Velarde application. Phloroglucinol is commercially available from various sources, such as from Sigma-Aldrich Co. (St Louis, Mo.), ACROS Organics/Fisher Scientific (Morris Plains, N.J.), or Pechiney World Trade USA (Stamford, Conn.). Phloroglucinol may also be produced by biosynthetic processes. The TNPG is filtered and washed with an aqueous, acidic solution, as described in the Velarde application, to remove contaminants. To reduce the sensitivity of the TNPG to impact and electrostatic discharge ("ESD"), the TNPG is stored with water until the alkoxylation reaction is conducted. After removing water, an organic solvent is added to the TNGP and the TNGP is alkoxylated to produce a 1,3,5-trialkoxy-2,4,6-trinitrobenzene compound, as described in the Velarde application. The TNGP is alkoxylated using a trialkyl orthoformate, such as trimethyl orthoformate, triethyl orthoformate ("TEOF"), tripropyl orthoformate, or mixtures thereof. By way of non-limiting example, if the TNGP is alkoxylated using TEOF, TETNB is formed. The 1,3,5-trialkoxy-2,4,6-trinitrobenzene compound is dissolved in an organic solvent to form a 1,3,5-trialkoxy-2,4,6-trinitrobenzene/organic solvent solution.

The 1,3,5-trialkoxy-2,4,6-trinitrobenzene/organic solvent solution may be washed in situ with water to remove nonvolatile impurities and to react with excess (unreacted) alkoxylating agent, as described in the Velarde application. The nonvolatile impurities may include, but are not limited to, inorganic salts, such as sodium chloride or nitrate salts, or partially alkoxylated trinitrobenzene compounds, such as mono- or di-alkoxylated trinitrobenzene compounds. An excess of water may be added to the 1,3,5-trialkoxy-2,4,6-trinitrobenzene/organic solvent solution, such as greater than approximately six equivalents of water. To neutralize acidic species, such as partially alkoxylated trinitrobenzene compounds, a caustic solution is used to wash, in situ, the 1,3,5-trialkoxy-2,4,6-trinitrobenzene/organic solvent solution. The caustic solution may be an aqueous solution that includes from approximately 0.5% to approximately 5.0% of a caustic agent, such as sodium hydroxide ("NaOH"). However, other caustic agents, such as other metal hydroxides, may also be used including, but not limited to, potassium hydroxide, lithium hydroxide, sodium carbonate, sodium bicarbonate, potassium carbonate, or potassium bicarbonate. The water also reacts with excess alkoxylating agent, producing volatile byproducts, such as ethanol, ethyl formate, ethyl acetate, diethyl ether, and mixtures thereof. The volatile byproducts remain in solution in the 1,3,5-trialkoxy-2,4,6-trinitrobenzene/organic solvent solution and may be removed by the distillation.

Alternating water washes and caustic solution washes may be conducted to remove substantially all of the nonvolatile impurities and the excess alkoxylating agent. Aqueous layers produced by the water washes and the caustic solution washes contain the nonvolatile impurities and the unreacted alkoxylating agent, which may be discarded. Organic layers produced during the wash include the volatile byproducts, which may be removed by distillation. This in situ washing of the 1,3,5-trialkoxy-2,4,6-trinitrobenzene/organic solvent solution increases the washing efficiencies and the purity of the 1,3,5-trialkoxy-2,4,6-trinitrobenzene compared to external crystal washing. As a result, the purity of the TATB is increased. After removing the impurities and excess alkoxylating agent, the 1,3,5-trialkoxy-2,4,6-trinitrobenzene/organic solvent solution may be dried to produce the 1,3,5-trialkoxy-2,4,6-trinitrobenzene compound. However, if the organic solvent is compatible with the conditions of the subsequent amination reaction, the 1,3,5-trialkoxy-2,4,6-trinitrobenzene compound may remain in solution.

The 1,3,5-trialkoxy-2,4,6-trinitrobenzene compound may then be aminated to produce TATB. While specific examples herein describe the 1,3,5-trialkoxy-2,4,6-trinitrobenzene compound as TETNB, the 1,3,5-trialkoxy-2,4,6-trinitrobenzene compound may be 1,3,5-trimethoxy-2,4,6-trinitrobenzene, 1,3,5-tripropoxy-2,4,6-trinitrobenzene, combinations thereof, or combinations of TETNB with at least one of 1,3,5-trimethoxy-2,4,6-trinitrobenzene and 1,3,5-tripropoxy-2,4,6-trinitrobenzene. To achieve the TATB having comparable properties to legacy TATB and improved properties compared to the TATB produced by the Velarde process, the amination reaction may be conducted at increased temperature and pressure conditions relative to the reaction conditions used during the amination reaction of the Velarde process. The 1,3,5-trialkoxy-2,4,6-trinitrobenzene compound may be dissolved in an organic solvent that is substantially non-reactive with an aminating agent under the conditions of the amination reaction. The organic solvent may be a non-polar, aromatic solvent, such as toluene, mesitylene, a xylene, or combinations thereof. The xylene may be o-, m-, p-xylene, or combinations thereof. The organic solvent may also be a polar, non-protic organic solvent, such as sulfolane, DMSO, DMF, n-methyl pyrrolidone ("NMP"), ethyl acetate ("EtOAc"), or combinations thereof. The organic solvent may also include a mixture of at least one non-polar, aromatic solvent with water or at least one polar, non-protic organic solvent with water. The organic solvent may also be a mixture of one of the above-mentioned non-polar, aromatic solvents and one of the above-mentioned polar, non-protic organic solvents. In one embodiment, the organic solvent is toluene. The ratio of the weight of 1,3,5-trialkoxy-2,4,6-trinitrobenzene compound to the volume of organic solvent may be within a range of from 1:5 to 1:30.

The 1,3,5-trialkoxy-2,4,6-trinitrobenzene compound solution may be placed in a pressure vessel, which is sealed. The pressure vessel may be configured to apply and maintain a desired temperature and pressure to the vessel contents. By way of non-limiting example, the pressure vessel may be a Parr reactor. Before adding the aminating agent, the 1,3,5-trialkoxy-2,4,6-trinitrobenzene compound solution may be heated to a temperature of between approximately 30° C. and approximately 110° C. For example, the temperature may be between approximately 60° C. and approximately 100° C. or between approximately 80° C. and approximately 100° C. Heating the 1,3,5-trialkoxy-2,4,6-trinitrobenzene compound solution to a temperature greater than approximately 120° C. increases the production of impurities, such as ADAP or EDATB, during the reaction. In one embodiment, the 1,3,5-trialkoxy-2,4,6-trinitrobenzene compound solution is heated to a temperature of approximately 90° C. During the heating, the 1,3,5-trialkoxy-2,4,6-trinitrobenzene compound solution may be stirred to maintain the 1,3,5-trialkoxy-2,4,6-trinitrobenzene in solution.

After the 1,3,5-trialkoxy-2,4,6-trinitrobenzene compound solution has equilibrated, the aminating agent may be introduced into the sealed, pressure vessel. The aminating agent may be ammonia (liquid or gaseous) or ammonium hydroxide (aqueous ammonia). The aminating agent and the 1,3,5-trialkoxy-2,4,6-trinitrobenzene compound may react to produce a product mixture that includes TATB. The aminating agent may be added to the pressure vessel such that the pressure vessel is overpressurized. After venting the pressure vessel to the atmosphere, the pressure vessel may be resealed and addition of the aminating agent resumed. The aminating agent may be reacted with the 1,3,5-trialkoxy-2,4,6-trinitrobenzene compound under pressure, such as a pressure of from approximately 30 psig to approximately 120 psig. For instance, the pressure vessel may be maintained at a system pressure of from approximately 40 psig to approximately 100 psig, or from approximately 40 psig to approximately 60 psig. The temperature and pressure may be maintained within the above-mentioned ranges during the amination reaction.

To achieve complete amination, an excess of the aminating agent may be used, such as greater than approximately one molar excess, relative to the 1,3,5-trialkoxy-2,4,6-trinitrobenzene compound. The aminating agent may be introduced into the pressure vessel over a short duration, such as approximately one minute. However, the aminating agent may be added to the pressure vessel over longer durations depending on whether small scale or production scale amounts of TATB are to be produced. The flow of the aminating agent into the pressure vessel may then be stopped. However, additional aminating agent may be added to the pressure vessel, as needed, due to leakage or consumption during the amination reaction. The 1,3,5-trialkoxy-2,4,6-trinitrobenzene compound and the aminating agent may be reacted in the pressure vessel with stirring for an amount of time sufficient to produce TATB. The 1,3,5-trialkoxy-2,4,6-trinitrobenzene and the aminating agent may be reacted for an amount of time ranging from approximately 2 hours to approximately 8 hours, such as from approximately 4 hours to approximately 6 hours.

The product mixture in the pressure vessel may then be cooled, such as to a temperature of less than or equal to approximately 60° C. After cooling, the pressure vessel may be released to atmospheric pressure. A solid material (i.e., TATB) may be present in the pressure vessel as a precipitate. The product mixture may be removed from the pressure vessel and water added to the product mixture. The aqueous layer may be removed and discarded, and the solid material filtered, yielding the TATB as a yellow crystalline product. The TATB may be washed to remove impurities, and dried. The wash may be conducted using distilled water, isopropanol, or combinations thereof.

The TATB produced by an embodiment of the invention may have a yield of greater than approximately 65% based on the 1,3,5-trialkoxy-2,4,6-trinitrobenzene compound. The yield may range from approximately 68.4% to 99.5% based on the 1,3,5-trialkoxy-2,4,6-trinitrobenzene compound. The purity of the TATB produced by the above-mentioned method may be greater than approximately 97%, as measured by HPLC. For instance, the purity of the TATB produced using toluene as the organic solvent may range from approximately 99.1% to 99.7%, while the purity of the TATB using other organic solvents, such as sulfolane, mesitylene, ethyl acetate, or xylene, may range from approximately 97.6% to 99.6%. In addition to TATB, when toluene is used as the organic solvent, the above-mentioned method may produce small amounts of ADAP and/or EDATB, such as less than approximately 2.3%. In one embodiment, the above-mentioned method produces 99.7% TATB and 0.3% ADAP. The density of TATB produced by an embodiment of the invention may range from approximately 1.90 g/ml to approximately 1.91 g/ml. The TATB produced by an embodiment of the invention may have a thermal stability, as measured by the temperature of DSC onset, of from approximately 369.8° C. to approximately 380° C.

Figure 2:
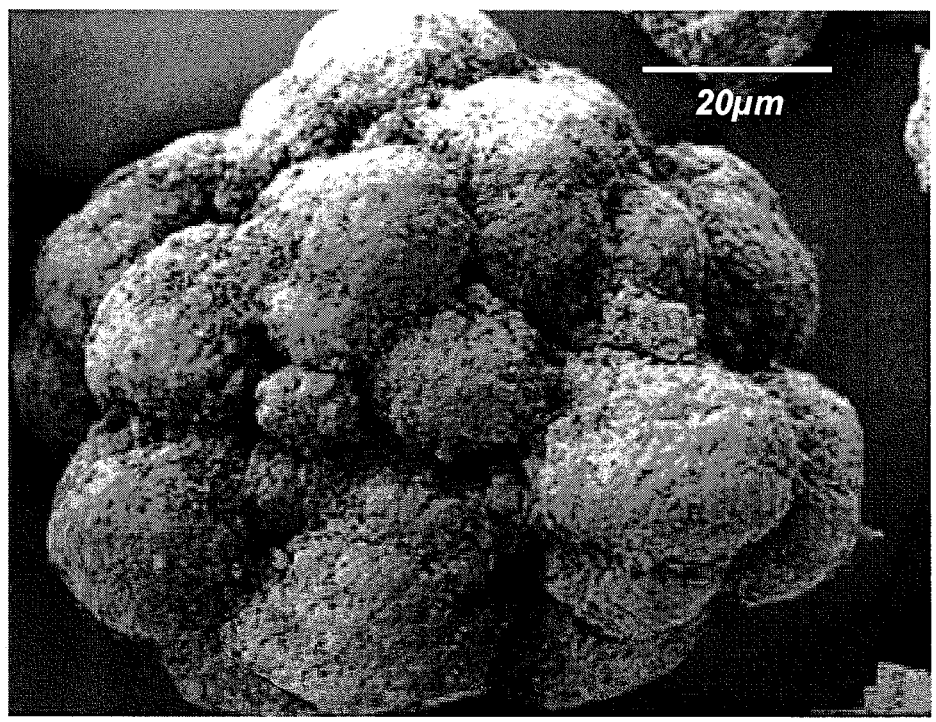
FIG. 2 is an SEM of TATB produced by the Velarde process.
Figure 3:
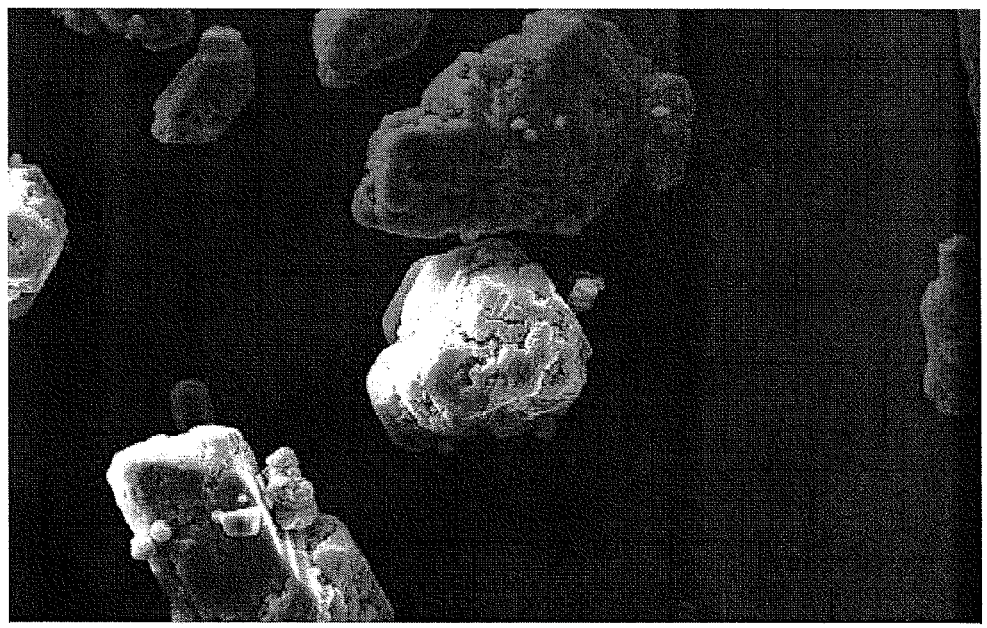
FIG. 3 is an SEM of legacy TATB crystals, produced by the process described in U.S. Pat. No. 4,032,377.

The TATB produced by an embodiment of the invention may form crystals having a substantially defect-free crystal structure, as shown in FIG. 1. The TATB crystals have a plate-like appearance. In contrast, the TATB produced by the Velarde process may form amorphous agglomerates exhibiting a cauliflower-like appearance, as shown in FIG. 2. The TATB crystals produced as described above may also include fewer defects than TATB crystals produced by the Velarde process. In comparison, the legacy TATB, which is produced by the process described in U.S. Pat. No. 4,032,377 to Benziger, also has a substantially defect-free crystal structure, as shown in FIG. 3. The density of each of the TATBs may be used to determine the percentage of defects in the TATB. The TATB produced by an embodiment of the invention has a density of 1.91 g/ml, as measured by gas pycnometry. In contrast, the theoretical maximum density (TMD) of TATB is 1.937 g/ml (as determined by x-ray crystallography and described in "The Insensitive High Explosive Triaminotrinitrobenzene (TATB): Development and Characterization-1888 to 1994," Brigitta M. Dobratz, August 1995). The Velarde TATB has a density of 1.8355 g/ml and the legacy TATB has a density between 1.9173 g/ml and 1.9181 g/ml (as described in Hoffman et al., "Comparison of New and Legacy TATBs," Journal of Ener. Mat. 26:139-162 (2008)). The percentage of defects in each of the TATBs is calculated as follows: [(TMD-sample density)/TMD]×100. The percentage of defects in the TATB produced by an embodiment of the invention is 1.4%, the percentage of defects in the Velarde TATB is 5.2%, and the percentage of defects in the legacy TATB is 1.0%.

To further improve at least one of the yield and purity of the desired morphology of the crystals, the 1,3,5-trialkoxy-2,4,6-trinitrobenzene compound solution may be seeded with ammonium chloride. Alternatively, the 1,3,5-trialkoxy-2,4,6-trinitrobenzene compound solution may be seeded with crystals of legacy TATB.

The TATB produced by an embodiment of the invention may be of increased purity compared to TATB produced by the Velarde process and be of a purity more comparable to that of the legacy TATB. The impurities (ADAP and EDATB) produced by an embodiment of the invention may also be reduced compared to those produced by the Velarde process. The density of the TATB produced by an embodiment of the invention may be comparable to that of the legacy TATB and substantially greater than the density of the TATB produced by the Velarde process. The TATB produced by an embodiment of the invention may have increased thermal stability compared to TATB produced by the Velarde process and thermal stability more comparable to that of the legacy TATB.

The mean particle size of the TATB produced by an embodiment of the invention may range from approximately 10 µm to approximately 35 µm, such as from approximately 20 µm to approximately 30 µm. To provide optimal characteristics for formulation processing, the mean particle size of the TATB may be from approximately 40 µm to approximately 50 µm. While the mean particle size of the TATB produced by an embodiment of the invention may be smaller than is desirable, it is believed that the mean particle size may increase when the reaction quantities are scaled up, such as during a pilot or production-scale phase.

Without being bound to a particular theory, it is believed that conducting the amination reaction in one of the organic solvents mentioned above and utilizing a temperature and pressure within the ranges mentioned above maintains the solubility of intermediate reaction products during the amination reaction. During the amination reaction, the intermediate reaction products include a 1-amino-3,5-dialkoxy-2,4,6-trinitrobenzene compound, a 1,3-diamino-5-trialkoxy-2,4,6-trinitrobenzene compound, TATB, or combinations thereof. The amination of the 1,3,5-trialkoxy-2,4,6-trinitrobenzene compound is believed to occur in a stepwise fashion in that the alkoxy groups are sequentially replaced with amine groups. As the 1,3,5-trialkoxy-2,4,6-trinitrobenzene compound is aminated, producing first a mono-amino derivative, then a di-amino derivative, and, finally, TATB, the solubility of these reaction products in the organic solvent decreases. The 1-amino-3,5-dialkoxy-2,4,6-trinitrobenzene compound is more soluble in the organic solvent than the 1,3-diamino-5-trialkoxy-2,4,6-trinitrobenzene compound, which is more soluble in the organic solvent than TATB. However, due to the temperature and pressure conditions within the pressure vessel, the 1-amino-3,5-dialkoxy-2,4,6-trinitrobenzene compound, the 1,3-diamino-5-trialkoxy-2,4,6-trinitrobenzene compound, or the TATB remain substantially soluble in the organic solvent during the amination reaction. By balancing the nucleation of crystals, crystal growth, and complete amination of the 1,3,5-trialkoxy-2,4,6-trinitrobenzene compound, TATB crystals having the desired morphology may be produced. Through appropriate selection of organic solvent, reaction temperature, and reaction pressure, formation of the desired TATB crystal structure may be achieved.

In contrast to the method of the invention, in the Velarde process, a solution including the 1,3,5-trialkoxy-2,4,6-trinitrobenzene compound is cooled to a temperature of from approximately −5° C. to approximately 5° C. before adding the amination agent. The aminating agent, such as ammonia, is more soluble in the cooled solution including the 1,3,5-trialkoxy-2,4,6-trinitrobenzene compound, enabling a more concentrated solution of ammonia to be produced at ambient pressure. After the amination reaction is substantially complete, the reactor is sealed and the temperature of the reaction mixture is increased to from approximately −33° C. to approximately 50° C. to ensure complete reaction of the 1,3,5-trialkoxy-2,4,6-trinitrobenzene compound to TATB. In addition to these temperature differences, the pressure vessel in the Velarde process is pressurized only after the amination reaction is substantially complete.

The amination reaction of the invention may also be conducted without an organic solvent, in a so-called "solventless" amination reaction. Instead of utilizing an organic solvent, the aminating agent, such as ammonia or ammonium hydroxide, may be used to form a suspension of the 1,3,5-trialkoxy-2,4,6-trinitrobenzene compound. The suspension of the 1,3,5-trialkoxy-2,4,6-trinitrobenzene compound and the aminating agent may be sealed in a pressure vessel and heated to a temperature of approximately 100° C. (if the aminating agent is ammonium hydroxide), or to a temperature of approximately 60° C. (if the aminating agent is ammonia), with stirring. The amination reaction may be conducted at atmospheric pressure, or the pressure vessel may be pressurized, such as at a pressure of from approximately 40 psig to approximately 60 psig. The 1,3,5-trialkoxy-2,4,6-trinitrobenzene compound may be reacted with ammonia or ammonium hydroxide for from approximately 2 hours to approximately 6 hours. The yield of TATB produced by the solventless reaction may be greater than approximately 90%, such as from approximately 93.8% to approximately 100%. The purity of the TATB produced by the solventless reaction may be greater than approximately 97.9%. Since the particle size of the TATB produced by the solventless reactions is small, it is believed that the TATB may be extremely insensitive. The yield of TATB produced by the solventless reaction may range from approximately 93% to approximately 100%.

The following examples serve to explain embodiments of the present invention in more detail. These examples are not to be construed as being exhaustive, exclusive or otherwise limiting as to the scope of this invention.

EXAMPLES

TETNB was produced at ATK Space Systems (Brigham City, Utah). The organic solvents, ammonia, and ammonium hydroxide were purchased from commercial sources, such as from Sigma-Aldrich Co. (St Louis, Mo.).

The properties shown in Tables 1-3 were measured or determined by conventional techniques, which are not described in detail herein. The TATB purity was measured by high pressure liquid chromatography ("HPLC"). Thermal stability was measured by differential scanning calorimetry ("DSC") using a temperature ramp rate of 20° C./minute. The thermal stability is reported as the temperature of the onset of decomposition. Morphological properties were determined by viewing crystals of the TATB using Scanning Electron Microscopy ("SEM"). The mean particle size was measured using a MICROTRAC® particle size analyzer. The density of the TATB was measured by gas pycnometry. Chemical analysis was measured by conventional techniques.

Example 1

Synthesis of TATB using Ammonia at 90° C. and 60 psig

TETNB (25.0 grams, 72.4 mmol) was dissolved in 250 ml of toluene and added to a 300 ml Parr reactor. The reactor was sealed and the contents heated with slow stirring to 90° C. and allowed to equilibrate. Gaseous ammonia was added to the reactor such that there was 5 psig of overpressure. The reactor was carefully vented to atmosphere and then resealed. Ammonia addition was resumed such that the total reactor pressure was approximately 60 psig. The reaction was stirred at this pressure and temperature for 4 hours, at which point the reactor was cooled. When the contents of the reactor reached less than or equal to approximately 50° C., the reactor was vented to the atmosphere. The contents of the reactor were transferred to a beaker and 50 ml of distilled water was added with stirring. The yellow crystalline product was filtered on a Buchner funnel and washed with distilled water. The yellow crystalline product was dried in a heated vacuum oven. The yellow crystalline product was determined to be TATB. Various properties of the TATB are reported in Tables 1-3 as Sample 2395-97.

Example 2

Synthesis of TATB at 90° C. and 60 psig

TETNB (5.0 grams, 14.5 mmol) was dissolved in 50 ml toluene and added to a Parr reactor. The reactor was sealed and the contents were heated with slow stirring to 90° C. and allowed to equilibrate. Gaseous ammonia was added to the reactor such that there was 5 psig of overpressure. The reactor was carefully vented to atmosphere and then resealed. Ammonia addition was resumed such that the total reactor pressure was approximately 60 psig. The reaction was stirred at this pressure and temperature for 2.0 hours, at which point the reactor was cooled. When the contents of the reactor reached less than or equal to approximately 50° C., the reactor was vented to the atmosphere. The contents of the reactor were transferred to a beaker and 15 ml of distilled water was added with stirring. The yellow crystalline product was filtered on a Buchner funnel and washed with distilled water. The yellow crystalline product was dried in a heated vacuum oven. Various properties of the TATB are reported in Tables 1-3 as Sample 2395-59.

Example 3

Synthesis of TATB at 90° C. and 60 psig

TETNB (5.0 grams, 14.5 mmol) was dissolved in 50 ml toluene and added to a Parr reactor. The reactor was sealed and the contents were heated with slow stirring to 90° C. and allowed to equilibrate. Gaseous ammonia was added to the reactor such that there was 5 psig of overpressure. The reactor was carefully vented to atmosphere and then resealed. Ammonia addition was resumed such that the total reactor pressure was approximately 60 psig. The reaction was stirred at this pressure and temperature for 4.0 hours, at which point the reactor was cooled. When the contents of the reactor reached less than or equal to approximately 50° C., the reactor was vented to the atmosphere. The contents of the reactor were transferred to a beaker and a volume of distilled water was added with stirring. The yellow crystalline product was filtered on a Buchner funnel and washed with distilled water. The yellow crystalline product was dried in a heated vacuum oven. Various properties of the TATB are reported in Tables 1-3 as Sample 2395-84.

Example 4

Synthesis of TATB at 90° C. and 60 psig

TETNB (5.0 grams, 14.5 mmol) was dissolved in 25 ml toluene, filtered through a bed of CELITE®, and added to a Parr reactor. The reactor was sealed and the contents were heated with slow stirring to 90° C. and allowed to equilibrate. Gaseous ammonia was added to the reactor such that there was 5 psig of overpressure. The reactor was carefully vented to atmosphere and then resealed. Ammonia addition was resumed such that the total reactor pressure was approximately 60 psig. The reaction was stirred at this pressure and temperature for 4.0 hours, at which point the reactor was cooled. When the contents of the reactor reached less than or equal to approximately 50° C., the reactor was vented to the atmosphere. The contents of the reactor were transferred to a beaker and 10 ml of distilled water was added with stirring. The yellow crystalline product was filtered on a Buchner funnel and washed with distilled water. The yellow crystalline product was dried in a heated vacuum oven. Various properties of the TATB are reported in Tables 1-3 as Sample 2440-16.

Example 5

Synthesis of TATB at 90° C. and 60 psig

TETNB (5.0 grams, 14.5 mmol) was dissolved in 100 ml toluene and added to a Parr reactor. The reactor was sealed and the contents were heated with slow stirring to 90° C. and allowed to equilibrate. Gaseous ammonia was added to the reactor such that there was 5 psig of overpressure. The reactor was carefully vented to atmosphere and then resealed. Ammonia addition was resumed such that the total reactor pressure was approximately 60 psig. The reaction was stirred at this pressure and temperature for 4.0 hours, at which point the reactor was cooled. When the contents of the reactor reached less than or equal to approximately 50° C., the reactor was vented to the atmosphere. The contents of the reactor were transferred to a beaker and 20 ml of distilled water was added with stirring. The yellow crystalline product was filtered on a Buchner funnel and washed with distilled water. The yellow crystalline product was dried in a heated vacuum oven. Various properties of the TATB are reported in Tables 1-3 as Sample 2440-17.

Example 6

Synthesis of TATB at 90° C. and 60 psig in Toluene/2% $H_2O$

TETNB (5.0 grams, 14.5 mmol) was dissolved in 50 ml of toluene, the solution was added to a Parr reactor, and 1 ml of distilled water was added to the solution in the reactor. The reactor was sealed and the contents were heated with slow stirring to 90° C. and allowed to equilibrate. Gaseous ammonia was added to the reactor such that there was 5 psig of overpressure. The reactor was carefully vented to atmosphere and then resealed. Ammonia addition was resumed such that the total reactor pressure was approximately 60 psig. The reaction was stirred at this pressure and temperature for 4.0 hours, at which point the reactor was cooled. When the contents of the reactor reached less than or equal to approximately 50° C., the reactor was vented to the atmosphere. The contents of the reactor were transferred to a beaker and 10 ml of distilled water was added with stirring. The yellow crystalline product was filtered on a Buchner funnel and washed with distilled water. The yellow crystalline product was dried in a heated vacuum oven. Various properties of the TATB are reported in Tables 1-3 as Sample 2440-18.

Example 7

Synthesis of TATB at 90° C. and 60 psig using Ammonium Chloride Seeds

TETNB (5.0 grams, 14.48 mmol) was dissolved in 50 ml of toluene and added to a Parr reactor. Approximately 10 mg of solid ammonium chloride was added to the reactor. The reactor was sealed and the contents were heated with slow stirring to 90° C. and allowed to equilibrate. Gaseous ammonia was added to the reactor such that there was 5 psig of overpressure. The reactor was carefully vented to atmosphere and then resealed. Ammonia addition was resumed such that the total reactor pressure was approximately 60 psig. The reaction was allowed to stir at this pressure and temperature for 4 hours, at which point the reactor was cooled. When the contents of the reactor reached less than or equal to approximately 50° C., the reactor was vented to the atmosphere. The contents of the reactor were transferred to a beaker and 10 ml of distilled water was added with stirring. The yellow crystalline product was filtered on a Buchner funnel and washed with distilled water. The yellow crystalline product was dried in a heated vacuum oven.

Example 8

Synthesis of TATB at 90° C. and 60 psig using Legacy TATB Seeds

TETNB (5.0 grams, 14.48 mmol) was dissolved in 50 ml toluene and added to a Parr reactor. A few crystals of legacy TATB were added to the reactor. The reactor was sealed and the contents were heated with slow stirring to 90° C. and allowed to equilibrate. Gaseous ammonia was added to the reactor such that there was 5 psig of overpressure. The reactor was carefully vented to atmosphere and then resealed. Ammonia addition was resumed such that the total reactor pressure was approximately 60 psig. The reaction was allowed to stir at this pressure and temperature for 4 hours, at which point the reactor was cooled. When the contents of the reactor reached less than or equal to approximately 50° C., the reactor was vented to the atmosphere. The contents of the reactor were transferred to a beaker and 10 ml of distilled water was added with stirring. The yellow crystalline product was filtered on a Buchner funnel and washed with distilled water. The yellow crystalline product was dried in a heated vacuum oven. Various properties of the TATB are reported in Tables 1-3 as Sample 2440-01.

Example 9

Synthesis of TATB at 60° C. and 60 psig

TETNB (5.0 grams, 14.48 mmol) was dissolved in 50 ml of toluene and added to a Parr reactor. The reactor was sealed and the contents were heated with slow stirring to 60° C. and allowed to equilibrate. Gaseous ammonia was added to the reactor such that there was 5 psig of overpressure. The reactor was carefully vented to atmosphere and then resealed. Ammonia addition was resumed such that the total reactor pressure was approximately 60 psig. The reaction was stirred at this pressure and temperature for 4 hours, at which point the reactor was cooled. When the contents of the reactor reached less than or equal to approximately 50° C., the reactor was vented to the atmosphere. The contents of the reactor were transferred to a beaker and 10 ml of distilled water was added with stirring. The yellow crystalline product was filtered on a Buchner funnel and washed with distilled water. The product was dried in a heated vacuum oven. The yellow crystalline was determined to be TATB.

Example 10

Synthesis of TATB at 30° C. and 60 psig

TETNB (5.0 grams, 14.48 mmol) was dissolved in 50 ml of toluene and added to a Parr reactor. The reactor was sealed and the contents were heated with slow stirring to 30° C. and allowed to equilibrate. Gaseous ammonia was added to the reactor such that there was 5 psig of overpressure. The reactor was carefully vented to atmosphere and then resealed. Ammonia addition was resumed such that the total reactor pressure was approximately 60 psig. The reaction was stirred at this pressure and temperature for 2 hours, at which point the reactor was cooled. When the contents of the reactor reached less than or equal to approximately 50° C., the reactor was vented to the atmosphere. The contents of the reactor were transferred to a beaker and 10 ml of distilled water was added with stirring. The yellow crystalline product was filtered on a Buchner funnel and washed with distilled water. The yellow crystalline product was dried in a heated vacuum oven. Various properties of the TATB are reported in Tables 1-3 as Sample 2395-57.

Example 11

Synthesis of TATB at 150° C. and 60 psig

TETNB (10 grams, 29.0 mmol) was dissolved in 105 ml toluene and added to a Parr reactor. The reactor was sealed and the contents were heated with slow stirring to 150° C. and allowed to equilibrate. Gaseous ammonia was added to the reactor such that there was 5 psig of overpressure. The reactor was carefully vented to atmosphere and then resealed. Ammonia addition was resumed such that the total reactor pressure was approximately 60 psig. The reaction was stirred at this pressure and temperature for 2.5 hours, at which point the reactor was cooled. When the contents of the reactor reached less than or equal to approximately 50° C., the reactor was vented to the atmosphere. The contents of the reactor were transferred to a beaker and a volume of distilled water was added with stirring. The yellow crystalline product was filtered on a Buchner funnel and washed with distilled water. The yellow crystalline product was dried in a heated vacuum oven. Various properties of the TATB are reported in Tables 1-3 as Sample 2322-32.

Example 12

Synthesis of TATB at 145° C. and 60 psig

TETNB (10 grams, 29.0 mmol) was dissolved in 100 ml toluene and added to a Parr reactor. The reactor was sealed and the contents were heated with slow stirring to 145° C. and allowed to equilibrate. Gaseous ammonia was added to the reactor such that there was 5 psig of overpressure. The reactor was carefully vented to atmosphere and then resealed. Ammonia addition was resumed such that the total reactor pressure was approximately 60 psig. The reaction was stirred at this pressure and temperature for 2.0 hours, at which point the reactor was cooled. When the contents of the reactor reached less than or equal to approximately 50° C., the reactor was vented to the atmosphere. The contents of the reactor were transferred to a beaker and a volume of distilled water was added with stirring. The yellow crystalline product was filtered on a Buchner funnel and washed with distilled water. The yellow crystalline product was dried in a heated vacuum oven. Various properties of the TATB are reported in Tables 1-3 as Sample 2322-34.

Example 13

Synthesis of TATB at 120° C. and 60 psig

TETNB (10 grams, 29.0 mmol) was dissolved in 100 ml toluene and added to a Parr reactor. The reactor was sealed and the contents were heated with slow stirring to 120° C. and allowed to equilibrate. Gaseous ammonia was added to the reactor such that there was 5 psig of overpressure. The reactor was carefully vented to atmosphere and then resealed. Ammonia addition was resumed such that the total reactor pressure was approximately 60 psig. The reaction was stirred at this pressure and temperature for 2.0 hours, at which point the reactor was cooled. When the contents of the reactor reached less than or equal to approximately 50° C., the reactor was vented to the atmosphere. The contents of the reactor were transferred to a beaker and a volume of distilled water was added with stirring. The yellow crystalline product was filtered on a Buchner funnel and washed with distilled water. The yellow crystalline product was dried in a heated vacuum oven. Various properties of the TATB are reported in Tables 1-3 as Sample 2395-53.

Example 14

Synthesis of TATB at 100° C. and 40 psig using Ammonium Hydroxide

TETNB (5.0 grams, 14.48 mmol) was dissolved in 50 ml of toluene and added to a Parr reactor along with 50 ml of ammonium hydroxide. The reactor was sealed and the contents were heated with slow stirring to 100° C. and allowed to equilibrate. The total reactor pressure was approximately 40 psig. The reaction was allowed to stir at this pressure and temperature for 2 hours, at which point the reactor was cooled. When the contents of the reactor reached less than or equal to approximately 50° C., the reactor was vented to the atmosphere. The contents of the reactor were transferred to a beaker and 10 ml of distilled water was added with stirring. The yellow crystalline product was filtered on a Buchner funnel and washed with distilled water. The yellow crystalline product was dried in a heated vacuum oven. Various properties of the TATB are reported in Tables 1-3 as Sample 2395-72.

Example 15

Synthesis of TATB at 100° C. and 40 psig using Ammonium Hydroxide

TETNB (10 grams, 29.0 mmol) was added to a Parr reactor along with 50 ml ammonium hydroxide. The reactor was sealed and the contents were heated with slow stirring to 100° C. and allowed to equilibrate. The total reactor pressure was approximately 40 psig. The reaction was allowed to stir at this pressure and temperature for 2 hours, at which point the reactor was cooled. When the contents of the reactor reached less than or equal to approximately 50° C., the reactor was vented to the atmosphere. The yellow crystalline product was filtered on a Buchner funnel and washed with distilled water. The yellow crystalline product was dried in a heated vacuum oven. Various properties of the TATB are reported in Tables 1-3 as Sample 2395-69.

Example 16

Synthesis of TATB at 0° C. using Toluene/Sulfolane

TETNB (2.0 grams, 5.79 mmol) was dissolved in 8 mL of toluene and 2 ml sulfolane in a round-bottom flask with stir bar. The reaction mixture was cooled to 0° C. Ammonia was bubbled through the reaction mixture for 1 hour. The yellow crystalline product was filtered on a Buchner funnel and washed with distilled water. The product was dried in a heated vacuum oven. Various properties of the TATB are reported in Tables 1-3 as Sample 2395-43.

Example 17

Synthesis of TATB at 30° C. and 60 psig using Mesitylene

TETNB (10.0 grams, 28.96 mmol) was dissolved in 100 ml of mesitylene and added to a Parr reactor. The reactor was sealed and gaseous ammonia was added to the reactor such that there was 5 psig of overpressure. The reactor was heated to 30° C. The reactor was carefully vented to atmosphere and then resealed. Ammonia addition was resumed such that the total reactor pressure was approximately 60 psig. The reaction was allowed to stir at this pressure and temperature for 2 hours. The reactor was vented to the atmosphere. The contents of the reactor were transferred to a beaker and 100 ml of distilled water was added with stirring. The yellow crystalline product was filtered on a Buchner funnel and washed with distilled water. The yellow crystalline product was dried in a heated vacuum oven. Various properties of the TATB are reported in Tables 1-3 as Sample 2395-55.

Example 18

Synthesis of TATB at 30° C. and 60 psig using Xylenes

TETNB (10.0 grams, 28.96 mmol) was dissolved in 100 ml of xylenes (≧98.5% o-, m-, and p-xylene and ethylbenzene) and added to a Parr reactor. The reactor was sealed and gaseous ammonia was added to the reactor such that there was 5 psig of overpressure. The reactor was heated to 30° C. The reactor was carefully vented to atmosphere and then resealed. Ammonia addition was resumed such that the total reactor pressure was approximately 60 psig. The reaction was stirred at this pressure and temperature for 2 hours. The reactor was vented to the atmosphere. The contents of the reactor were transferred to a beaker and 100 ml of distilled water was added with stirring. The yellow crystalline product was filtered on a Buchner funnel and washed with distilled water. The yellow crystalline product was dried in a heated vacuum oven. Various properties of the TATB are reported in Tables 1-3 as Sample 2395-60.

Example 19

Synthesis of TATB at 30° C. and 60 psig using Ethyl Acetate

TETNB (1.0 grams, 2.90 mmol) was dissolved in 10 ml of ethyl acetate and added to a Parr reactor. The reactor was sealed and gaseous ammonia was added to the reactor such that there was 5 psig of overpressure, then was vented to the atmosphere. Ammonia addition was resumed such that the total reactor pressure was approximately 60 psig. The reaction was allowed to stir at pressure and temperature for 2 hours. The reactor was vented to the atmosphere. The contents of the reactor were transferred to a beaker and 10 ml of distilled water was added with stirring. The yellow crystalline product was filtered on a Buchner funnel and washed with distilled water. The yellow crystalline product was dried in a heated vacuum oven. Various properties of the TATB are reported in Tables 1-3 as Sample 2395-58.

Example 20

Synthesis of TATB at 30° C. and 60 psig using Sulfolane

TETNB (5.0 grams, 14.48 mmol) was dissolved in 50 ml of sulfolane and added to a Parr reactor. The reactor was sealed and heated to 30° C. Gaseous ammonia was added to the reactor such that there was 5 psig of overpressure. The reactor was carefully vented to atmosphere and then resealed. Ammonia addition was resumed such that the total reactor pressure was approximately 60 psig. The reaction was stirred at this pressure and temperature for 4 hours. The reactor was vented to the atmosphere. The contents of the reactor were transferred to a beaker and 50 ml of distilled water was added with stirring. The yellow crystalline product was filtered on a Buchner funnel and washed with distilled water. The yellow crystalline product was dried in a heated vacuum oven. Various properties of the TATB are reported in Tables 1-3 as Sample 2395-86.

Example 21

Synthesis of TATB at 90° C. and 60 psig using Sulfolane

TETNB (5.0 grams, 14.48 mmol) was dissolved in 50 ml of sulfolane and added to a Parr reactor. The reactor was sealed and heated to 90° C. Gaseous ammonia was added to the reactor such that there was 5 psig of overpressure. The reactor was carefully vented to atmosphere and then resealed. Ammonia addition was resumed such that the total reactor pressure was approximately 60 psig. The reaction was stirred at pressure and temperature for 5.5 hours. The reactor was vented to the atmosphere. The contents of the reactor were transferred to a beaker and 50 ml of distilled water was added with stirring. The yellow crystalline product was filtered on a Buchner funnel and washed with distilled water. The yellow crystalline product was dried in a heated vacuum oven. Various properties of the TATB are reported in Tables 1-3 as Sample 2395-91.

Example 22

Synthesis of TATB at 30° C. using Sulfolane

TETNB (1.0 g, 2.9 mmol) was dissolved in 10 ml sulfolane and added to a round-bottom flask with a stir bar. The round-bottom flask was heated to 35° C. A few crystals of legacy TATB were added. Ammonia was bubbled through the reaction mixture for 1 hour. The yellow crystalline product was filtered on a Buchner funnel and washed with distilled water. The yellow crystalline product was dried in a heated vacuum oven. Various properties of the TATB are reported in Table 2 as Sample 2395-52.

Example 23

Synthesis of TATB at 35° C. using Sulfolane

TETNB (1.0 g, 2.9 mmol) was dissolved in 30 ml sulfolane and added to a round-bottom flask with a stir bar. The round-bottom flask was heated to 35° C. Ammonia was bubbled through the reaction mixture for 1 hour. The yellow crystalline product was filtered on a Buchner funnel and washed with distilled water. The yellow crystalline product was dried in a heated vacuum oven. Various properties of the TATB are reported in Table 2 as Sample 2395-51.

Example 24

Synthesis of TATB at 100° C. using Neat Ammonium Hydroxide

TETNB (10.0 grams, 28.96 mmol) was added to a Parr reactor with 100 ml of ammonium hydroxide. The reactor was sealed and heated to 100° C. for 2 hours with stirring. At this temperature the pressure was approximately 80 psig. The reactor was cooled and then vented to the atmosphere. The contents of the reactor were transferred to a beaker and 100 ml of distilled water was added with stirring. The yellow crystalline product was filtered on a Buchner funnel and washed with distilled water. The yellow crystalline product was dried in a heated vacuum oven. Various properties of the TATB are reported in Tables 1-3 as Sample 2395-67.

Example 25

Synthesis of TATB at Room Temperature and 60 psig using Neat Ammonia

TETNB (1.0 grams, 2.90 mmol) was added to a Parr reactor at room temperature (approximately 25° C.). Ammonia gas was added such that the total reactor pressure was approximately 60 psig and the reaction was stirred for 18 hours. The reactor was vented and 10 ml of distilled water was added. The yellow crystalline product was filtered on a Buchner funnel and washed with distilled water. The yellow crystalline product was dried in a heated vacuum oven. Various properties of the TATB are reported in Tables 1-3 as Sample 2395-74.

Example 26

Synthesis of TATB at Room Temperature and 60 psig using Neat Ammonia

TETNB (5.0 grams, 14.48 mmol) was added to a Parr reactor at room temperature. Ammonia gas was added such that the total reactor pressure was approximately 60 psig and the reaction was stirred for 72 hours at room temperature. The reactor was vented and 10 ml of distilled water was added. The yellow crystalline product was filtered on a Buchner funnel and washed with distilled water. The yellow crystalline product was dried in a heated vacuum oven. Various properties of the TATB are reported in Tables 1-3 as Sample 2395-77.

Example 27

Effect of Temperature and Concentration on TATB Purity and Yield, Impurity Production, Particle Size and Thermal Stability The effect of temperature on the yield of TATB and production of impurities (ADAP and EDATB) was determined and is reported in Table 1. All reactions were conducted at a pressure of 60 psig $NH_3$ in a Parr bomb pressure vessel. Reactions conducted at approximately 90° C. exhibited the optimal balance of high purity and yield of TATB and low amounts of ADAP and EDATB. Higher temperatures, such as those above approximately 140° C., resulted in the increased formation of ADAP.

TABLE 1

Comparison of TATB Yield, Purity, Particle Size, and Thermal Stability as a Factor of Temperature and TETNB Concentration.

| Sample | Time (h) | Temp (° C.) | ml Toluene: g TETNB | Yield (%) | % TATB | % ADAP | % EDATB | Mean Particle Size (μm) | 1st Onset DSC (° C.) |
|---|---|---|---|---|---|---|---|---|---|
| 2322-32 | 2.5 | 150 | 10:1 | 82.3 | 60.5% | 39.5% | 0.0% | 29.85 | 289 |
| 2232-34 | 2.0 | 145 | 10:1 | 90.9 | 43.8% | 56.2% | 0.0% | 11.65 | 290.7 |
| 2395-53 | 2.0 | 120 | 10:1 | 81.2 | 89.6% | 10.4% | 0.0% | 32.81 | 373.4 |
| 2395-59 | 2.0 | 90 | 10:1 | 91.4 | 99.3% | 0.3% | 0.4% | 25.75 | 374.5 |
| 2395-84 | 4.0 | 90 | 10:1 | 84.5 | 99.5% | 0.2% | 0.3% | 22.53 | 369.8 |
| 2395-97 | 4.0 | 90 | 10:1 | 99.5 | 99.5% | 0.5% | 0.0% | n/a | 378.0 |
| 2440-01 (seeded) | 4.0 | 90 | 10:1 | 74.3 | 99.7% | 0.3% | 0.0% | n/a | 380 |
| 2395-57 | 2.0 | 30 | 10:1 | 88.7 | 98.5% | 0.3% | 1.2% | 16.33 | 368.7 |
| 2440-16 | 4.0 | 90 | 5:1 | 80.0 | 98.9% | 0.9% | 0.2% | 13.82 | 272 |
| 2440-17 | 4.0 | 90 | 20:1 | 85.8 | 99.1% | 0.9% | 0.0% | 21.78 | 274 |
| 2440-18 | 4.0 | 90 | 1% $H_2O$ | 75.7 | 99.3% | 0.5% | 0.2% | 23.59 | 273 |

The effect of TETNB concentration on the yield and purity of TATB and production of impurities (ADAP and EDATB) was determined and is reported in Table 1. When a solution of 1 g of TETNB in 10 ml toluene was used at a given reaction temperature (90° C.), the TATB yield was greater than approximately 74% and the TATB purity was greater than approximately 99%. When a more concentrated solution of TETNB in toluene was used at the same reaction temperature, the purity of the resulting TATB was lower and the impurity content (ADAP and EDATB) was greater. When a less concentrated solution of TETNB in toluene was used at the same reaction temperature, a higher purity of TATB resulted but the impurity content was greater. In addition, a higher concentration of TETNB in toluene produced TATB having a small particle size.

Example 28

Effect of Organic Solvent on TATB Purity and Yield, Impurity Production, Particle Size and Thermal Stability The effect of different organic solvents, or no organic solvent, on the yield of TATB and production of impurities (ADAP and EDATB) was determined and is reported in Table 2.

TABLE 2

Comparison of TATB Yield, Purity, Particle Size, and Thermal Stability as a Function of Solvent.

| Sample | Solvent | Pressure (psig) | Temp (° C.) | Yield (%) | % TATB | ADAP | EDATB | 50% Size (μm) | 1st Onset DSC (° C.) |
|---|---|---|---|---|---|---|---|---|---|
| 2395-43 | Toluene/Sulfolane | 0 | 0 | 92.5 | 97.7% | 0.6% | 1.7% | 14.46 | 368 |
| 2395-52 | Sulfolane 10 ml/g | 0 | 30 | 99.2 | 99.1% | 0.3% | 0.7% | N/A | N/A |
| 2395-51 | Sulfolane 30 ml/g | 0 | 35 | 68.4 | 99.0% | 0.2% | 0.7% | N/A | N/A |
| 2395-86 | Sulfolane 10 ml/g | 40-60 | 30 | 91.4 | 98.9% | 0.5% | 0.7% | 8.47 | 367 |
| 2395-91 | Sulfolane 10 ml/g | 40-60 | 90 | 86.7 | 99.6% | 0.1% | 0.3% | 20.33 | 372 |
| 2395-55 | Mesitylene | 0 | 30 | 89.7 | 98.4% | 0.3% | 1.2% | 27.8 | 367.8 |
| 2395-60 | Xylene | 0 | 30 | 93.8 | 98.5% | 0.4% | 1.2% | 22.9 | 353.6 |
| 2395-69 | NH$_4$OH | ~40 | 100 | 90.5 | 98.7% | 1.1% | 0.2% | Trimodal | 373 |
| 2395-72 | Toluene/NH$_4$OH (5 g:50:50) | ~40 | 100 | 92.5 | 98.9% | 0.7% | 0.0% | 12.46 | 374.5 |
| 2395-74 | None (NH$_3$) | 60 | (18 h) | 93.8 | 99.6% | 0.3% | 0.2% | Small | 379 |
| 2395-77 | None (NH$_3$) | 60 | (72 h) 100 | 97.9% | 1.2% | 1.1% | Small | 365 |
| 2395-58 | EtOAc | 0 | RT | 63 | 97.6% | 0.8% | 1.6% | — | — |

As indicated by the results in Table 2, other organic solvents, such as mesitylene, xylene, ethyl acetate, or sulfolane, could be used to synthesize TATB from TETNB. Investigating these organic solvents at additional temperatures and pressures of the amination reaction may further improve the properties of the resulting TATB. The results also show that the TATB could be synthesized from TETNB without a solvent present, such as by using neat ammonia or neat ammonium hydroxide.

Example 29

Comparison of TATB Produced by Various Processes

Various properties of TATB produced by the method of the invention are compared with those of legacy TATB and with TATB produced by the Velarde process ("Velarde TATB"). These results are shown in Table 3.

TABLE 3

Comparison of TATB Purity, Particle Size, and Thermal Stability.

| Sample | % TATB | % ADAP | % EDATB | Mean Particle Size (μm) | Density (gas pyc) | DSC Onset (° C.) | % C, % H, % N |
|---|---|---|---|---|---|---|---|
| 2395-59 | 99.3% | 0.3% | 0.4% | 25.75 | — | 374.5 | 28.21, 1.92, 32.00 |
| 2395-84 | 99.5% | 0.2% | 0.3% | 22.53 | — | 369.8 | 28.20, 1.89, 32.07 |
| 2395-97 | 99.5% | 0.5% | 0.0% | n/a | — | 378.0 | 28.14, 2.02, 32.04 |
| 2440-01 (seeded) | 99.7% | 0.3% | 0.0% | n/a | — | 380 | 28.11, 1.95, 32.03 |
| Velarde TATB | 97.60% | 1.80% | 0.60% | 54.3 | 1.83-1.84 | 368.9 | 29.02, 2.04, 31.44 |
| Legacy | 100% | 0% | 0% | 70.4 | 1.91-1.92 | >378 | 27.92, |

TABLE 3-continued

Comparison of TATB Purity, Particle Size, and Thermal Stability.

| Sample | % TATB | % ADAP | % EDATB | Mean Particle Size (μm) | Density (gas pyc) | DSC Onset (° C.) | % C, % H, % N |
|---|---|---|---|---|---|---|---|
| TATB | | | | | | | 2.34, 32.55 |

Samples 2395-59, 2395-84, 2395-97, and 2440-01, which were produced by an embodiment of the invention, had a higher purity than that of the Velarde TATB and included less ADAP and EDATB impurities. This TATB also had a higher DSC onset, indicating its greater thermally stability. The TATB decomposed about 0.9° C. to about 9.1° C. higher than the Velarde TATB. The TATB produced by an embodiment of the invention was comparable in purity to the legacy TATB. Samples 2395-59, 2395-84, 2395-97, and 2440-01 also had a comparable density compared to that of the legacy TATB.

The crystal morphologies of the TATB produced by an embodiment of the invention, the Velarde TATB, and the legacy TATB are shown in FIGS. 1-3, respectively. The TATB crystals produced by an embodiment of the invention had a substantially defect-free crystal structure, as shown in FIG. 1, similar to the crystal structure of legacy TATB shown in FIG. 3. In contrast, the Velarde TATB forms agglomerates with a cauliflower-like morphology, as shown in FIG. 2.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the scope of the invention as defined by the following appended claims and their legal equivalents.

What is claimed is:

1. A method of producing 1,3,5-triamino-2,4,6-trinitrobenzene, comprising:
   heating a 1,3,5-trialkoxy-2,4,6-trinitrobenzene compound solution consisting of a 1,3,5-trialkoxy-2,4,6-trinitrobenzene compound and at least one solvent to a temperature of from approximately 30° C. to approximately 110° C. in a pressure vessel; and
   pressurizing the pressure vessel with an aminating agent to a pressure of from approximately 30 pounds per square inch to approximately 120 pounds per square inch to react the 1,3,5-trialkoxy-2,4,6-trinitrobenzene compound in the heated 1,3,5-trialkoxy-2,4,6-trinitrobenzene compound solution with the aminating agent to produce a 1,3,5-triamino-2,4,6-trinitrobenzene solution.

2. The method of claim 1, wherein heating a 1,3,5-trialkoxy-2,4,6-trinitrobenzene compound solution consisting of a 1,3,5-trialkoxy-2,4,6-trinitrobenzene compound and at least one solvent to a temperature of from approximately 30° C. to approximately 110° C. in a pressure vessel comprises heating 1,3,5-trimethoxy-2,4,6-trinitrobenzene, 1,3,5-triethoxy-2,4,6-trinitrobenzene, 1,3,5-tripropoxy-2,4,6-trinitrobenzene, or combinations thereof in the at least one solvent.

3. The method of claim 1, wherein heating a 1,3,5-trialkoxy-2,4,6-trinitrobenzene compound solution consisting of a 1,3,5-trialkoxy-2,4,6-trinitrobenzene compound and at least one solvent to a temperature of from approximately 30° C. to approximately 110° C. in a pressure vessel comprises heating the 1,3,5-trialkoxy-2,4,6-trinitrobenzene compound in toluene, mesitylene, xylene, ethyl acetate, sulfolane, or combinations thereof.

4. The method of claim 1, wherein heating a 1,3,5-trialkoxy-2,4,6-trinitrobenzene compound solution consisting of a 1,3,5-trialkoxy-2,4,6-trinitrobenzene compound and at least one solvent to a temperature of from approximately 30° C. to approximately 110° C. in a pressure vessel comprises heating the 1,3,5-trialkoxy-2,4,6-trinitrobenzene compound solution to a temperature of from approximately 60° C. to approximately 110° C.

5. The method of claim 1, wherein heating a 1,3,5-trialkoxy-2,4,6-trinitrobenzene compound solution consisting of a 1,3,5-trialkoxy-2,4,6-trinitrobenzene compound and at least one solvent to a temperature of from approximately 30° C. to approximately 110° C. in a pressure vessel comprises heating the 1,3,5-trialkoxy-2,4,6-trinitrobenzene compound solution to a temperature of from approximately 80° C. to approximately 100° C.

6. The method of claim 1, wherein heating a 1,3,5-trialkoxy-2,4,6-trinitrobenzene compound solution consisting of a 1,3,5-trialkoxy-2,4,6-trinitrobenzene compound and at least one solvent to a temperature of from approximately 30° C. to approximately 110° C. in a pressure vessel comprises heating the 1,3,5-trialkoxy-2,4,6-trinitrobenzene compound solution to a temperature of approximately 90° C.

7. The method of claim 1, wherein pressurizing the pressure vessel with an aminating agent to a pressure of from approximately 30 pounds per square inch to approximately 120 pounds per square inch comprises pressurizing the pressure vessel with the aminating agent at a pressure of from approximately 40 pounds per square inch to approximately 100 pounds per square inch.

8. The method of claim 1, wherein pressurizing the pressure vessel with an aminating agent to a pressure of from approximately 30 pounds per square inch to approximately 120 pounds per square inch comprises pressurizing the pressure vessel with the aminating agent at a pressure of from approximately 40 pounds per square inch to approximately 60 pounds per square inch.

9. The method of claim 1, wherein pressurizing the pressure vessel with an aminating agent to a pressure of from approximately 30 pounds per square inch to approximately 120 pounds per square inch comprises pressurizing the pressure vessel with the aminating agent at a pressure of approximately 60 pounds per square inch.

10. The method of claim 1, wherein pressurizing the pressure vessel with an aminating agent comprises pressurizing the pressure vessel with ammonia or ammonium hydroxide.

11. The method of claim 1, further comprising cooling the 1,3,5-triamino-2,4,6-trinitrobenzene solution to precipitate the 1,3,5-triamino-2,4,6-trinitrobenzene.

12. The method of claim 11, further comprising washing the 1,3,5-triamino-2,4,6-trinitrobenzene with water or isopropanol.

13. A method of producing 1,3,5-triamino-2,4,6-trinitrobenzene, comprising:

heating a 1,3,5-triethoxy-2,4,6-trinitrobenzene solution consisting of 1,3,5-triethoxy-2,4,6-trinitrobenzene and toluene to a temperature of approximately 90° C. in a pressure vessel; and pressurizing the pressure vessel with ammonia to a pressure of approximately 60 pounds per square inch to react the 1,3,5-triethoxy-2,4,6-trinitrobenzene in the heated 1,3,5-triethoxy-2,4,6-trinitrobenzene solution to produce 1,3,5-triamino-2,4,6-trinitrobenzene.

14. A method of producing 1,3,5-triamino-2,4,6-trinitrobenzene, comprising:

introducing a 1,3,5-triethoxy-2,4,6-trinitrobenzene solution consisting of 1,3,5-triethoxy-2,4,6-trinitrobenzene and at least one solvent into a pressure vessel;

sealing the pressure vessel;

heating the 1,3,5-triethoxy-2,4,6-trinitrobenzene solution to a temperature of approximately 90° C.;

pressurizing the pressure vessel with ammonia to a total reactor pressure of approximately 60 pounds per square inch; and reacting the 1,3,5-triethoxy-2,4,6-trinitrobenzene with the ammonia to produce 1,3,5-triamino-2,4,6-trinitrobenzene.

15. The method of claim 3, wherein the at least one solvent further comprises water.

16. The method of claim 1, further comprising adding seed crystals to the pressure vessel.

* * * * *